United States Patent [19]

Tjoeng et al.

[11] Patent Number: 5,053,393
[45] Date of Patent: Oct. 1, 1991

[54] NOVEL PLATELET-AGGREGATION INHIBITOR

[75] Inventors: Foe S. Tjoeng, Manchester, Mo.; Larry P. Feigen, Wauconda, Ill.; Steven P. Adams, St. Charles, Mo.

[73] Assignees: Monsanto Co., St. Louis, Mo.; G. D. Searle & Co., Skokie, Ill.

[21] Appl. No.: 540,953

[22] Filed: Jun. 20, 1990

Related U.S. Application Data

[60] Continuation-in-part of Ser. No. 395,614, Aug. 18, 1989, abandoned, which is a division of Ser. No. 221,703, Jul. 20, 1988, Pat. No. 4,879,313.

[51] Int. Cl.$^5$ ............................................. A61K 31/21
[52] U.S. Cl. ..................................... 514/18; 514/616; 564/153; 564/157; 530/331
[58] Field of Search ..................... 514/20, 616, 18; 564/153, 157; 530/331

[56] References Cited

U.S. PATENT DOCUMENTS

| 4,051,141 | 9/1977 | Castaigne | 260/294.8 |
|---|---|---|---|
| 4,127,580 | 11/1978 | Braye | 546/114 |
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Rouslahti et al. | 623/11 |
| 4,661,111 | 4/1987 | Ruoslahti et al. | 623/11 |
| 4,683,291 | 7/1987 | Zimmerman et al. | 530/324 |
| 4,857,508 | 8/1989 | Adams et al. | 514/18 |
| 4,879,313 | 11/1989 | Tjoeng et al. | 514/20 |

OTHER PUBLICATIONS

Kloczewiak et al., Biochem., 23, 1767-1774 (1984).
Plow et al., Proc. Natl. Acad. Sci., 82, 8057-8061 (1984).
Ruggerri et al., Ibid., 83, 5708-5712 (1986).
Ginsberg et al., J. Biol. Chem., 260(7), 3931-3936 (1985).
Haverstick et al., Blood, 66(4), 946-952 (1985).

*Primary Examiner*—C. Warren Ivy
*Assistant Examiner*—Zinna Northington-Davis
*Attorney, Agent, or Firm*—Scott J. Meyer; James W. Williams, Jr.

[57] ABSTRACT

N-[8-[(Aminoiminomethyl)amino]-1-oxooctyl]-N-L-α-aspartyl-L-phenylanine is disclosed as a highly potent inhibitor of platelet aggregation.

5 Claims, 5 Drawing Sheets

NOVEL PLATELET-AGGREGATION INHIBITOR

CROSS-REFERENCE TO RELATED APPLICATIONS

This is a continuation-in-part of application Ser. No. 07/395,614, filed Aug. 18, 1989, now abandoned, which in turn is a division of application Ser. No. 07/221,703, filed July 20, 1988, now U.S. Pat. No. 4,879,313.

BACKGROUND OF THE INVENTION

This invention relates to a novel peptide mimetic compound having potent in vivo activity as an inhibitor of platelet aggregation.

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. These polypeptides include an internal amino acid sequence Arg-Gly-Asp-Ser (RGDS). Certain relatively short peptide fragments from the same molecule were found to promote cell attachment to a substrate when immobilized on the substrate or to inhibit attachment when in solubilized or suspended form. See U.S. Pat. Nos. 4 578,079 and 4,614,517. These peptides were defined as X-Arg-Gly-Asp-R-Y wherein
X=H or amino acid, R=Thr or Cys; and X-Arg-Gly-Asp-Ser-Y wherein
X=H or amino acid, Y=OH or amino acid.

In U.S. Pat. No. 4,683,291, inhibition of platelet function is disclosed with synthetic peptides designed to be high affinity antagonists of fibrinogen binding to platelets. These synthetic peptides have up to 16 amino acid residues with Arg-Gly-Asp-Val or Arg-Gly-Asp-Ser at the C-terminal.

Similar synthetic peptides which contain the Arg-Gly-Asp sequence and their use as inhibitors of fibrinogen binding to platelets are disclosed by Koczewiak et al., Biochem. 23, 1767–1774 (1984); Plow et al., Proc. Natl. Acad. Sci. 82, 8057–8061 (1985); Ruggeri et al., Ibid. 83, 5708–5712 (1986); Ginsberg et al., J. Biol. Chem. 260 (7), 3931–3936 (1985); Haverstick et al., Blood 66 (4), 946–952 (1985); and Ruoslahti and Pierschbacher, Science 238, 491–497 (1987). Still other such inhibitory peptides are disclosed in EP patent application Nos. 275,748 and 298,820.

In U.S. Pat. No. 4,857,508, certain novel tetrapeptide derivatives are disclosed which have enhanced activity as inhibitors of platelet aggregation. These tetrapeptide derivatives contain the sequence X-Gly-Asp-Y in which X and Y are defined to comprise a variety of organic moieties. An illustrative preferred example is Arg-Gly-Asp-(O-methyl-Tyr)-$NH_2$.

BRIEF DESCRIPTION OF THE INVENTION

In accordance with the present invention, a novel peptide mimetic compound is provided which has potent in vivo activity as an inhibitor of platelet aggregation. This inhibitor is believed to act by antagonizing interactions between fibrinogen and/or extracellular matrix proteins and the platelet gpIIb/IIIa receptor. The novel inhibitor compound of this invention has a guanidino group at the N-terminus, a pseudopeptide or peptide mimetic bond in the chain and a phenylalanine group at the C-terminus. This peptide mimetic compound can be represented by the following chemical structure:

$$H_2N-\underset{NH}{\overset{NH}{C}}-NH-(CH_2)_{7',6',5',4',3',2'}-\overset{O}{C}-NH-CH(CH_2COOH)-C(O)-NH-CH(CH_2-C_6H_5)-COOH$$

Its systematic name is N-[8-[(aminoiminomethyl)amino]-1-oxooctyl]-N-L-α-aspartyl-L-phenylalanine; but it is more conveniently referred to hereinafter as 8-guanidinooctanoyl-aspartyl-phenylalanine or by the shorthand term 8-GO-Asp-Phe.

The novel 8-GO-Asp-Phe peptide mimetic compound of the invention is demonstrated to have outstanding platelet aggregation inhibitory activity by the following results obtained in various in vitro and in vivo tests:

Directly inhibits the binding of $^{125}I$-fibrinogen to thrombin activated human platelets.

Inhibits aggregation of human and dog platelets in vitro to a variety of proaggregatory stimuli: Thrombin, collagen, ADP.

Induces a sustained antiplatelet effect during constant intravenous infusion.

Possesses a relatively short duration of action permitting rapid termination of antiplatelet effects if required by the clinical situation.

Exhibits no effects on human neutrophil elastase release or degranulation.

Lacks acute hemodynamic or electrocardiographic effects in dogs at infusion rates that are 10 times higher than those required to achieve 90% inhibition of platelet aggregation in this species.

Lacks CNS effects in mice at 0.5, 1, 2, and 24 hours following a dose of compound that was 20-fold greater than the rat antiplatelet $ED_{50}$.

When compared with the closely related 8-guanidino-octanoyl-Asp-2-(4-methoxyphenyl)-ethylamide (8-GO-Asp-MPE) described in U.S. Pat. No. 4,879,313, it is observed that the novel 8-GO-Asp-Phe unexpectedly has substantially increased solubility and potency. 8-GO-Asp-Phe is surprisingly about 5 to 15 fold more potent in vitro and about 5 fold more active in vivo than 8-GO-Asp-MPE.

Based on the foregoing test results, it is believed that the 8-GO-Asp-Phe will be useful in a variety of therapeutic interventions, for example, preventing re-occlusion following re-canalization procedures such as post fibrinolytic therapy, thrombolytic therapy, angioplasty and coronary bypass surgery. Other potential uses are for prevention of myocardial infarct, recurrent myocardial infarct, unstable angina, peripheral artery disease, cerebral ischemia, stroke and diseases of platelet hyperaggregability, and to prevent occlusion in hemodialysis, shunt procedures and to prevent progression of atherosclerosis.

The novel 8-GO-Asp-Phe has also been found to substantially shorten the time to reperfusion and to substantially prolong the time to achieve re-occlusion after lysis of a clot by administration of the thrombolytic agent t-PA in dogs. Thus, the compound should be useful for co-administration with t-PA in thrombolytic therapies.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which the figures are graphical representations as follows:

Figure 1:
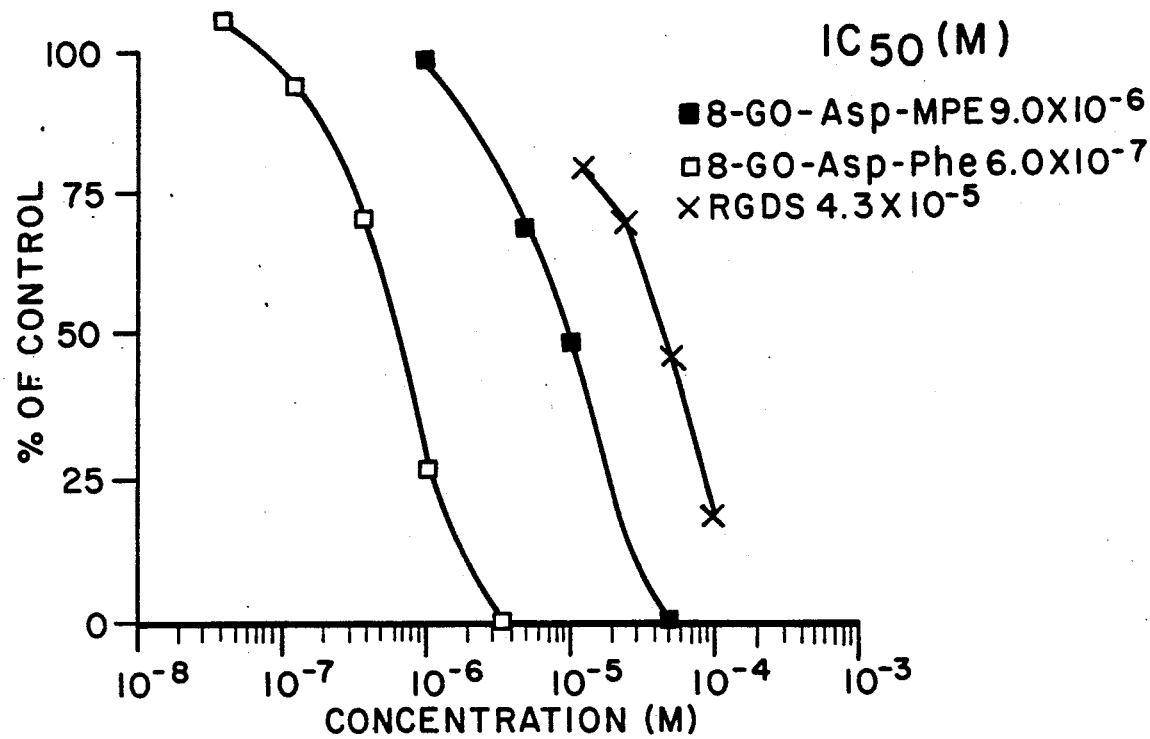
FIG. 1 shows the inhibition of fibrinogen binding to human washed platelets by the respective inhibitors 8-GO-Asp-Phe (□), 8-GO-Asp-MPE (■) and RGDS (X) in which the % of fibrinogen binding compared to control (without inhibitor) is plotted against the molar concentration (M) of the inhibitor.

The platelet aggregation inhibitor compound 8-GO-Asp-Phe can be prepared by various convenient procedures. Thus, it can be prepared by solid and solution phase methods analogous to the methods described in U.S. Pat. No. 4,879,313 for the preparation if 8-Guanidino-octanoyl-Asp-2-(4-methoxyphenyl)ethylamide (8-GO-Asp-MPE) except that the C-terminal 4methoxyphenyl ethylamide is replaced with phenylalanine.

In one useful procedure, the platelet aggregation inhibitor compound 8-GO-Asp-Phe was synthesized by coupling 8-guanidinooctanoic acid with aspartyl-phenylalanine methyl ester (aspartame) followed by saponification of the methyl ester with sodium hydroxide. The product crystallized from cold aqueous methanol (pH 4.0) and was subsequently recrystallized from aqueous methanol with an overall yield of 73%. In laboratory preparations, 8-guanidinooctanoic acid was prepared either by reaction of 8-aminooctanoic acid with 3,5-dimethylpyrazole-1-carboxamidine or from guanidine and 8-bromooctanoic acid.

Although specific methods of production are described herein, it will be appreciated that the 8-GO-Asp-Phe of this invention is not limited to any specific method of production.

The following examples will further illustrate the invention in greater detail although it will be appreciated that the invention is not limited to these specific examples.

EXAMPLE 1

A. 8-Guanidino-octanoic acid (8-GO)

3,5-dimethyl-pyrazole-1-carboxamidine (100 g; 0.5 Mole) and N,N-diisopropylethyl amine (DIEA) (65 g; 0.5 Mole) were suspended in dioxane (300 ml) and water (115 ml). 8-Amino-octanoic acid (48 cg; 0.3 Mole) was added to the mixture with stirring. The colorless solution was then refluxed for 2 days. The product was filtered and washed with water (3×50 ml).

The dried material weighed 60 g; FAB-MS: $(M+H)=202$.

B. 8-Guanidino-octanic acid. HCl (8-GO.HCl)

8-GO.HCl was prepared by lyophilizing 8-GO dissolved in one equivalent of 0.1 M HCl.

EXAMPLE 2

8-Guanidinooctanoic acid.HCl (39 g; 195 mmoles), disuccinimidylcarbonate (50 g; 195 mmoles) and 4-dimethylaminopyridine (2 g) were dissolved in pyridine/DMF (1:2; 350 ml). The reaction mixture was stirred at room temperature overnight. To this vigorously stirred solution was added a suspension of Asp-Phe-OMe (50 g; 169 mmoles) and sodium bicarbonate (15 g; 169 mmoles) in water (150 m)). The coupling reaction was complete in 20 hours as determined by analytical HPLC analysis. The mixture was evaporated *in vacuo* to an oily residue, which was dissolved in methanol (150 ml). To this solution (350 ml), stirring in an ice bath, was added 2.5 N NaOH (280 ml) and the stirring was continued for 5 hours at which point the reaction mixture was acidified to pH 4 with 4 N HCl (185 ml). The resulting solution was refrigerated to effect crystallization and the solid product was collected by filtration and air dried. The product was suspended in water (1.0 liter) with gentle heating and methanol (400 ml) was added until a clear solution was obtained. The product crystallized upon cooling to room temperature and was collected by filtration. This material was dried *in vacuo* over phosphorous pentoxide to yield 64 g of 8-GO-Asp-Phe product.

A portion of the crystalline product was purified by preparative reverse phase chromatography for analytical characterization.

Preparative reverse phase chromatography was performed with a Waters Prep LC-3000 system using a 4.5 ×30 cm column (15-20 μ particle size, μ-Bondapak). A 0.5 g sample of 8-GO-Asp-Phe dissolved in 10 ml of saturated NaHCO$_3$ was applied to the column and submitted to a solvent gradient of 5–20% CH$_3$CN (0.05% TFA) over 30 min at a flow rate of 80 ml/min. Product containing fractions were pooled and lyophilized. Product recovery was about 90%.

Analytical HPLC (Vydac C-18 column, 300 Å pore size; 15–40% CH$_3$CN/H$_2$O/0.05% TFA gradient over 25 minutes, 1.5 ml/min flow rate) with UV detection at 215 nM revealed a product that constitutes 99+% of the UV absorbing material.

FAB-MS identified a product with MW 463.54.

2-D NMR resonance assignments (500 MHz, DMSO-d6) are entirely consistent with the structure and are shown in Table 1.

Amino acid analysis indicated that 91% of the sample by weight contained phenylalanine and aspartic acid in equimolar ratios.

Elemental analysis: Calculated for C$_{22}$H$_{33}$N$_5$O$_6$; C: 57.0, H: 7.17, N: 15.1; Found: C: 56.8, H: 7.08, N: 15.0.

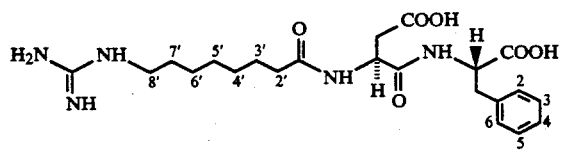

TABLE 1

| Chemical Shift Assignments of 8-guanidino-octanoyl-aspartyl-phenylalanine at 30° C. in DMSO d-6*. | | | | |
|---|---|---|---|---|
| residue | NH | αH | βH | other |
| Asp | 8.19 | 4.48 | 2.67, 2.42 | |
| Phe | 7.03 | 4.02 | 3.05, 2.95 | H2-6, 7.13 multiplet |
| 8-GO** | | | | H2' 2.12, 2.01; H3' 1.57, 1.34; H4' 1.10; H7' 1.33; H8' 2.97 guanidino NH 9.7, |

TABLE 1-continued

| Chemical Shift Assignments of 8-guanidino-octanoyl-aspartyl-phenylalanine at 30° C. in DMSO d-6*. | | | | |
|---|---|---|---|---|
| residue | NH | αH | βH | other |
| | | | | NH$_2$ 6.93. |

*ppm relative to DMSO (2.5 ppm).
**8-guanidino-octanoyl

EXAMPLE 3

8-GO-Asp-Phe was evaluated as a platelet aggregation inhibitory agent and compared with 8-guanidino-octanoyl-Asp-2-(4-methoxyphenyl)-ethylamide (8-GO-Asp-MPE) and/or RGDS with *in vitro* and *in vivo* assays as follows:

Fibrinogen Binding Assay

Fibrinogen binding was performed essentially as described by Plow et al., *Blood* 70, 110–115 (1987). Briefly, blood from human volunteers who had not taken any antiplatelet drugs in the previous two weeks was collected into 1/10th volume of CCD buffer (100 mM sodium citrate, 136 mM glucose, pH 6.5). The blood was centrifuged for 3 min at 1000×g and platelet rich plasma was transferred to a plastic tube with a plastic pipet and placed on ice. After 15 minutes, ½ volume of ice cold CCD buffer was added and the sample was centrifuged at 900×g for 10 min at 2° C. The supernatant was decanted and the platelet pellet was gently resuspended in ½ the original volume of ice cold modified Tyrode's buffer (137 mM NaCl, 2.6 mM KCl, 12 mM NaHCO$_3$, 5.5 mM glucose, 15 mM HEPES, 0.5% BSA, pH 7.4). After incubating for 30 minutes at 37° C., the platelet count was adjusted to 4×10$^8$ a platelets/ml with modified Tyrode's buffer. To platelet samples (1×10$^8$ platelets/ml) were added in sequence: ADP (10 μM), CaCl$_2$ (1 mM), test compound, and $^{125}$I-fibrinogen (0.3 μM) to the aforesaid final concentrations in a volume of 200 μl. The samples were incubated for 40 min at 37° C. and 50 μl aliquots were centrifuged at 8,000×g through a 20% sucrose pad (400 μl). The tubes were quick frozen and the tips containing the platelet pellet were cut and assayed for bound $^{125}$I-fibrinogen by gamma scintillation counting. Specific binding was determined in each test by subtracting from the total binding the amount $^{125}$I-fibrinogen bound in the presence of a 60-fold excess of unlabeled fibrinogen. The potency of test compounds (IC$_{50}$) was determined as the concentration of compound required to inhibit 50% of $^{125}$I-fibrinogen binding.

In-Vitro Human Platelet Aggregation in PRP

Healthy male or female donors who had not taken any antiplatelet drugs for at least 2 weeks were fasted for 8 hours prior to drawing blood; then 30 ml whole blood was collected using a butterfly needle and 30 cc plastic syringe with 3 ml of 0.129 M buffered sodium citrate (3.8%). The syringe was rotated carefully as blood was drawn to mix the citrate. Platelet-rich plasma (PRP) was prepared by centrifugation at 100×g for 10 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of $2-3 \times 10^8$ a platelets per ml. 400 μl of the PRP preparation and 50 μl of the compound to be tested or saline were preincubated for 1 minute at 37° C. in a Payton aggregometer (Payton Scientific, Inc., Buffalo, N.Y.). 50 μl of adenosine 5'diphosphate (ADP) (50 μM) was added to the cuvettes and the aggregation was monitored for 1 minute. All compounds are tested in duplicate. Results are calculated as follows: Percent of control =[(maximal OD minus initial OD of compound) divided by (maximal OD minus initial OD of control saline)]×100. The % inhibition=100−(percent of control).

In Vivo Rat Thrombocytopenia

Male rats [Charles River, CRL:CD(SD), 400–450 g] were used. The rats were anesthetized with Na pentobarbital (65 mg/kg, Vet Labs, Limited, Inc., Lenexa, Kans.). Two incisions were made to expose both jugular veins. Using an infusion pump (Harvard Apparatus, South Natick, Mass.) and a 5 cc syringe with a 19 g. butterfly, the test compound or vehicle was infused into the left jugular vein at a rate of 0.39 ml/min for 3 min. After 2 min of compound/vehicle infusion, collagen (60 μg/kg) (Helena Laboratories, Beaumont, Tex.) was injected with a one ml syringe into the right jugular vein. The body cavity was opened and the vena cava was exposed for blood sampling. One min after the collagen injection, compound infusion was stopped and blood was sampled from the vena cava (within 30 sec) with a 3 cc syringe containing 0.3 mg of 4.5% EDTA/-Tris (0.1 M) (pH 7.35) plus 150 μM indomethacin. Platelet rich plasma (PRP) was prepared by centrifuging the blood at 126×g for 10 min. Five μl of PRP was counted in 20 ml of Isoton® III (Coulter, isotonic solution) in a Coulter Counter.

Percent inhibition of collagen induced aggregation was calculated by comparison of the platelet counts in animals that were treated with test compound and collagen (a) with platelet counts for animals receiving no collagen (non-aggregated control) and (b) with platelet counts for animals receiving vehicle and collagen (aggregated control). $ED_{50}$s were calculated for the intravenously administered (i.v.) test compounds.

The results of these assays are as follows:

RESULTS

A. Binding of fibrinogen to platelets

8-GO-Asp-Phe inhibited the binding of $^{125}$I-fibrinogen to ADP stimulated washed human platelets. FIG. 1 illustrates that it inhibited with an $IC_{50}$ of $6.0 \times 10^{-7}$ M.

8-GO-Asp-Phe was approximately 5-fold more potent than 8-GO-Asp-MPE in inhibiting binding of fibrinogen to platelets and about 70 times more potent than RGDS. The shape of the binding inhibition curve was similar for all three compounds.

B. Inhibition of platelet aggregation in vitro

Figure 2:
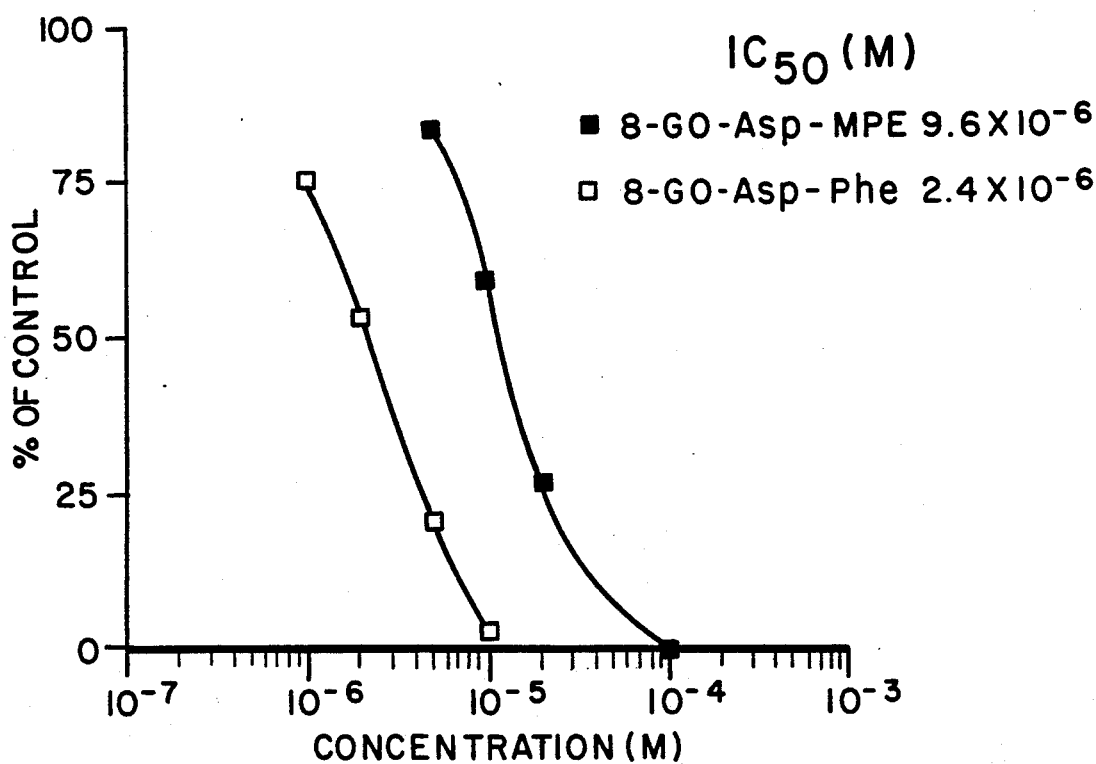
FIG. 2 shows the inhibition of ADP-induced platelet aggregation in human platelet rich plasma by 8-GO-Asp-Phe (□) and 8-GO-Asp-MPE (■) plotted as % of platelet aggregation compared to control (without inhibitor) versus the molar concentration (M) of inhibitor.
Figure 3:
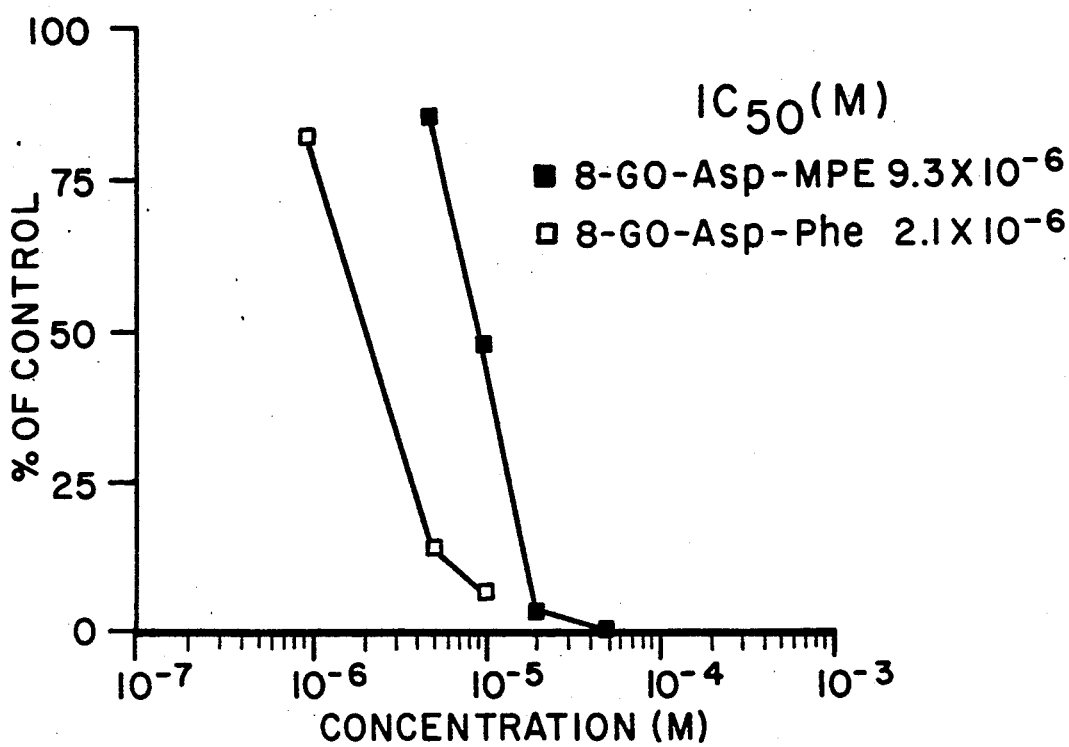
FIG. 3 shows the inhibition of collagen-induced platelet aggregation in dog platelet rich plasma by 8-GO-Asp-Phe (□) and 8-GO-Asp-MPE (■) plotted as in FIG. 2.

Platelet rich plasma (PRP) was prepared from freshly withdrawn blood samples of humans or dogs. PRP was then incubated with 8-GO-Asp-Phe or 8-GO-Asp-MPE for two minutes in an aggregometer cuvette at 37° C. after which either ADP (as is illustrated for human PRP in FIG. 2) or collagen (illustrated for dog PRP in FIG. 3) (Table 2) was added. The extent of aggregation was monitored by measuring light transmittance through the PRP solution. Both compounds inhibited platelet aggregation in a concentration dependent manner in human and dog PRP in response to ADP and collagen, respectively.

In both human and dog PRP 8-GO-Asp-Phe was approximately 5 fold more potent than 8-GO-Asp-MPE.

Figure 4:
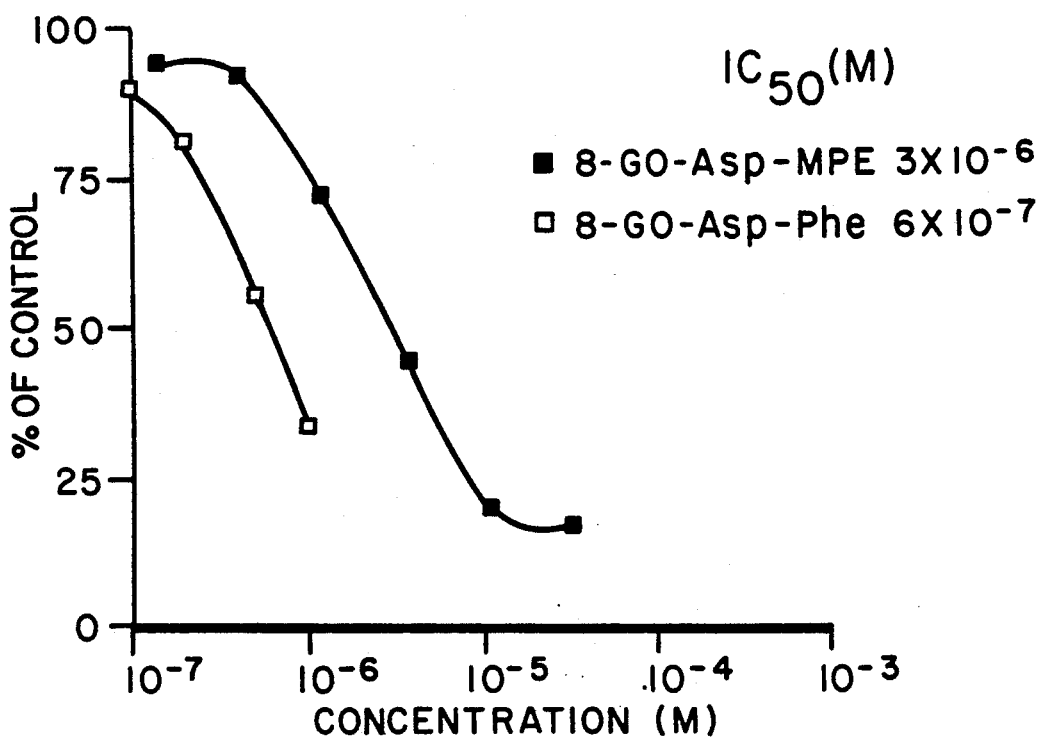
FIG. 4 shows the inhibition of thrombin-induced platelet aggregation in washed human platelets by 8-8-GO-Asp-Phe (⊔), 8-GO-Asp-MPE (■) Plotted as in FIG. 2.

Human PRP was also subjected to a washing procedure in order to remove plasma proteins prior to the aggregation assay. Washed platelets were then incubated with test compound in the cuvette and aggregated with thrombin (results are illustrated in FIG. 4, Table 2). 8-GO-Asp-Phe was 5 times more potent than 8-GO-Asp-MPE in inhibiting thrombin-induced aggregation in washed platelets.

TABLE 2

| Summary of in vitro Activity Inhibition of Platelet Aggregation by 8-GO-Asp—Phe and 8-GO-Asp—MPE in vitro: $IC_{50}$'s (M) | | |
| --- | --- | --- |
| | 8-GO-Asp—Phe | 8-GO-Asp—MPE |
| Human | | |
| PRP (ADP) | $2.4 \times 10^{-6}$ | $9.6 \times 10^{-6}$ |
| washed (thrombin) | $6.0 \times 10^{-7}$ | $3.0 \times 10^{-6}$ |
| Dog | | |
| PRP (collagen) | $2.1 \times 10^{-6}$ | $9.3 \times 10^{-6}$ |

In all cases in which 8-GO-Asp-Phe was found to be active in vitro, only aggregation was inhibited, whereas platelet shape change in response to the various agonist challenges was not blocked. Thus, the compound does not interfere with the process of platelet activation but rather blocks the aggregation process at the subsequent, fibrinogen binding step.

C. Inhibition of platelet aggregation in vivo

Collagen induced thrombocytopenia in the rat

Figure 5:
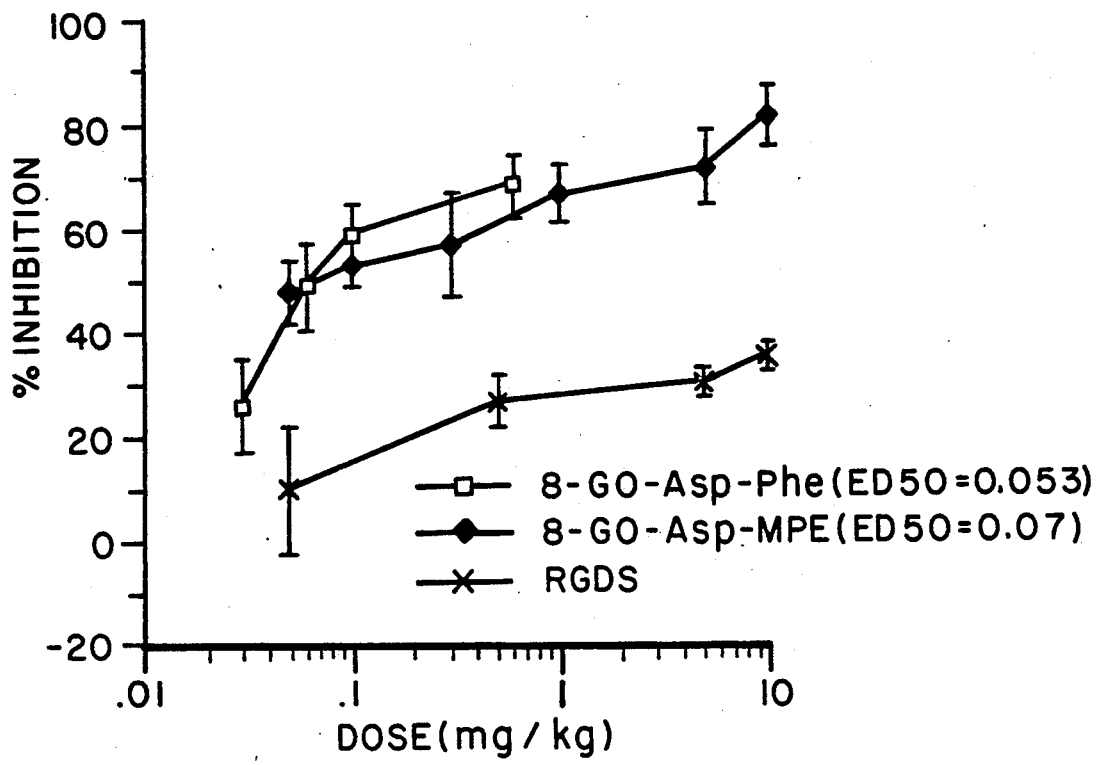
FIG. 5 shows the inhibition of collagen-induced thrombocytopenia in rat by the respective inhibitors 8-GO-Asp-Phe (⊔) 8-GO-Asp-MPE (■) and RGDS (X) in which the % inhibition of thrombocytopenia (decrease of platelet count) compared to control (without inhibitor) is plotted against the dose (ms/kg) of the inhibitor.

The number of platelets in blood withdrawn from rats after intravenous injection of collagen are significantly reduced compared to normal counts. The presence of collagen in the blood causes activation and aggregation of platelets. These aggregated platelet masses are cleared from the circulation by microvascular entrapment, accounting for the observed fall in platelet numbers. 8-GO-Asp-Phe, 8-GO-Asp-MPE or RGDS was infused intravenously into rats for two minutes prior to collagen injection, continued for an additional min after collagen injection and the effect on numbers of platelets was determined (FIG. 5).

8-GO-Asp-Phe inhibited collagen (60 μg/kg) induced thrombocytopenia in a dose dependent manner, with an $ED_{50}$ of 0.05 mg/kg. 8-GO-Asp-MPE was also effective at an $ED_{50}$ of 0.07 mg/kg. In contrast, RGDS did not inhibit aggregation by 50% at doses up to 10 mg/kg.

Figure 6:
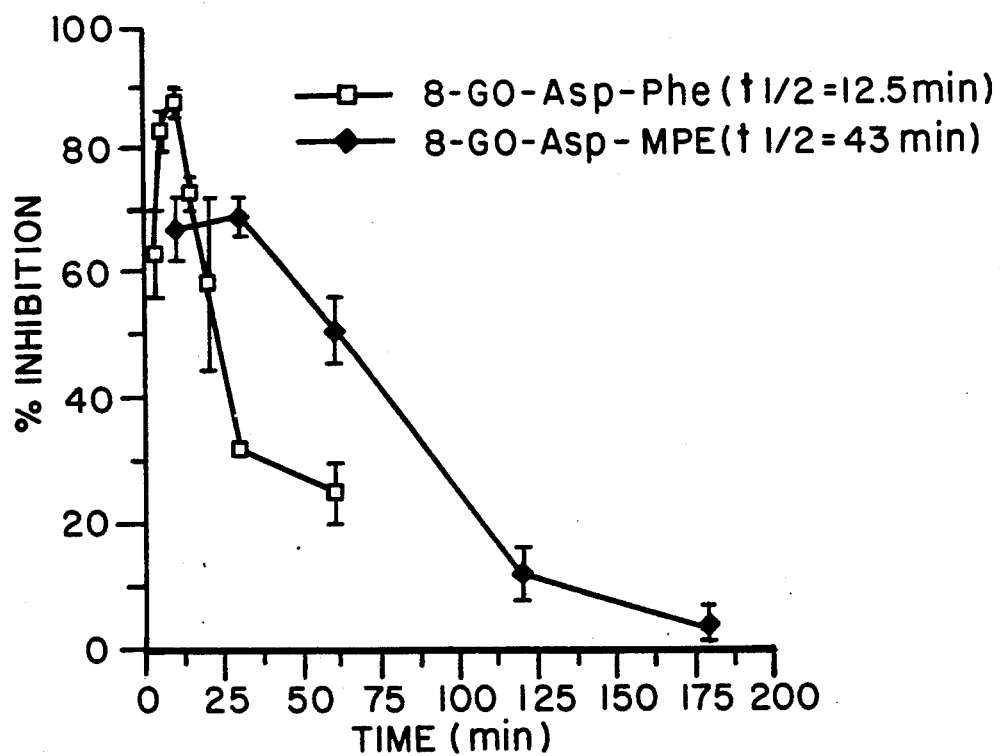
FIG. 6 shows the time course for inhibition of collagen-induced thrombocytopenia in rat by 8-GO-Asp-Phe (□) and 8-GO-Asp-MPE (■) in which % inhibition is plotted against time (min).

Intravenous administration of 0.10 mg/kg of 8-GO-Asp-Phe ($2 \times ED_{50}$), showed maximum activity 15 min after the end of a 3 min infusion and led to 90% inhibition of collagen-induced thrombocytopenia (FIG. 6).

Platelet aggregation inhibitory activity after 0.1 mg/kg 8-GO-Asp-Phe ($t_{\frac{1}{2}}$ at $2 \times ED_{50}$) declined with a half-life of 12 min. In comparison, 0.14 mg/kg 8-GO-Asp-MPE ($2 \times ED_{50}$) led to a 70% reduction in thrombocytopenia with a $t_{\frac{1}{2}}$ of 43 min.

D. Inhibition of collagen-induced, ex vivo, platelet aggregation in dogs

Figure 7:
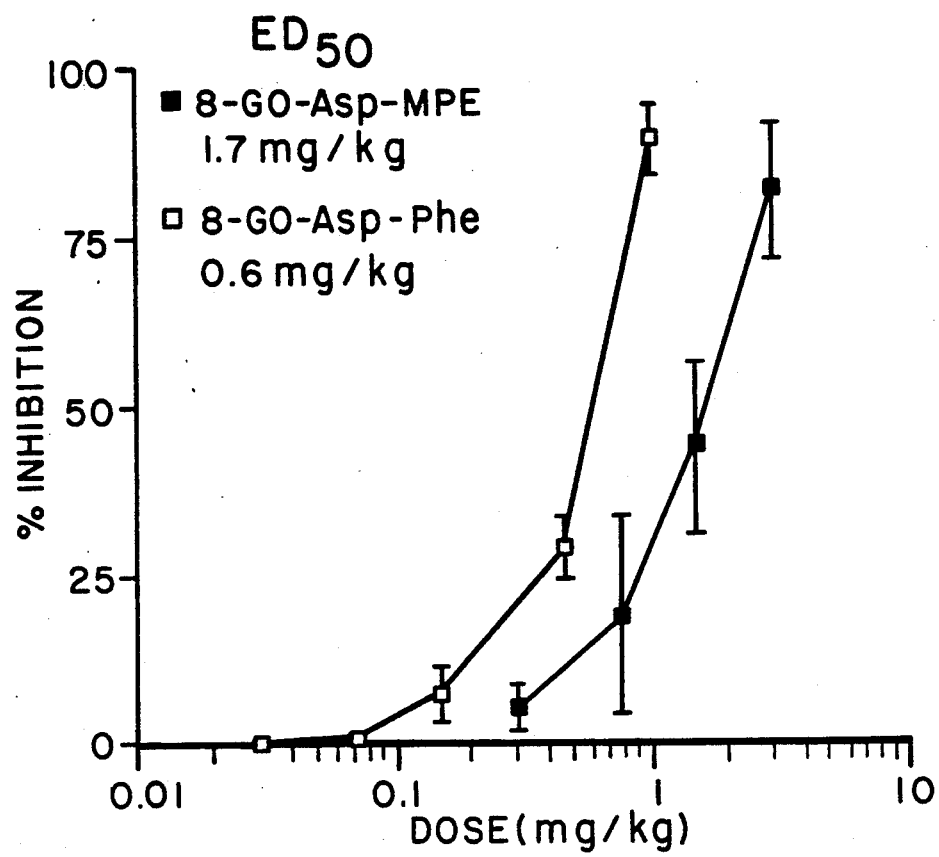
FIG. 7 shows the effect of 8-GO-Asp-Phe (□) and 8-GO-Asp-MPE (■) by IV bolus on ex vivo collagen-induced platelet aggregation in dogs where % of inhibition of platelet sample compared to control (without inhibitor) is plotted against the dose (mg/kg) of the inhibitor.
Figure 8:
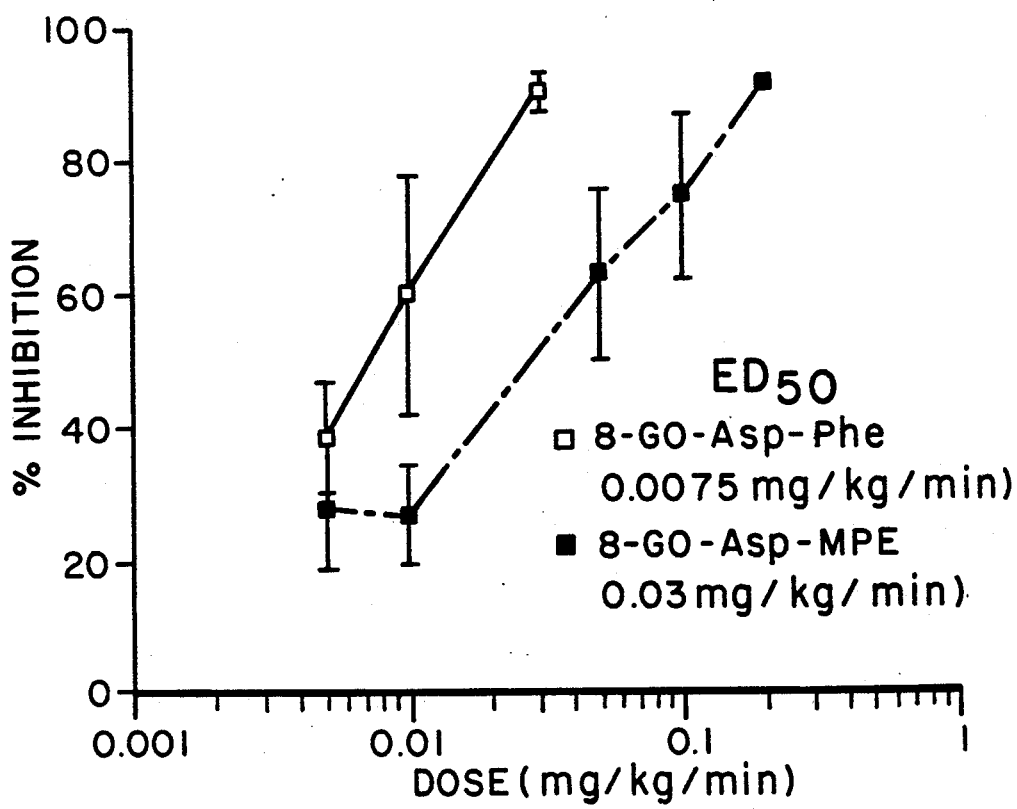
FIG. 8 shows the effect of IV infusion of 8-GO-Asp-Phe (□) and 8-GO-Asp-MPE (■) on ex vivo collagen-induced platelet aggregation in dogs plotted as in FIG. 7.

Dogs were anesthetized and received intravenous infusions of 8-GO-Asp-Phe. Before, during and after infusion of the compound at various dose rates, blood samples were taken, PRP prepared and platelet aggregatory responses to collagen were evaluated in an aggregometer. In separate studies-8-GO-Asp-Phe was administered as a bolus over 1 min (FIG. 7) or infused for 2 hrs (FIG. 8) to achieve steady state platelet responses.

8-GO-Asp-Phe produced dose-dependent inhibition of collagen-induced platelet aggregation in the dog with either protocol. With bolus injections, the $ED_{50}$ for 8-GO-Asp-Phe was 0.6 mg/kg, compared to the $ED_{50}$ of 1.7 mg/kg determined for 8-GO-Asp-MPE assessed 5 min after the injection (Because of the short half life of 8-GO-Asp-Phe activity was also assessed at 2 min post administration. 8-GO-Asp-Phe had an $ED_{50}$ of 0.30 mg/kg when measured at 2 min after injection). The $ED_{50}$ for steady state inhibition (determined by averaging the responses from 45 min to 2 hr) was 0.0075 mg/kg/min (compared to 0.03 mg/kg/min for 8-GO-Asp-MPE).

EXAMPLE 4

8-GO-Asp-Phe was evaluated as an, agent to shorten the time to reperfusion and to prolong the time to achieve re-occlusion after lysis of a clot by administration of the thrombolytic agent, tissue plasminogen activator (t-PA), in dogs. The following procedure was employed for this test:

Dogs weighing approximately 25 kg are anesthetized with pentobarbital, 30 mg/kg i.v. The left jugular vein is isolated and cannulated to provide a route for i.v. injections. The left carotid artery is cannulated for the purpose of measuring blood pressure. A left thoracotomy is performed through the fifth intercostal space. The pericadium is opened and a pericardial cradle is constructed using 00 silk sutures. The left anterior descending coronary artery (LADCA) is dissected free of its sheath for a distance of at least 3 cm. All side branches, except one large one, are ligated with 4-0 or 5-0 silk suture. An electromagnetic flow probe of appropriate size is applied to the proximal end of the isolated segment of LADCA. The preserved side branch is cannulated with a PE-50 catheter attached to a 23g needle adapter and a 3 way stopcock. A 2 mm wide plastic device made for wrapping wires is applied to the distal end of the segment. Several pieces of silk suture, size 2-0 and 4-0, (approximately 10 pieces) which can be removed are placed within the loop of the plastic band to provide adjustment of flow after the loop is tightened around the vessel.

Flow through the segment is reduced by tightening the plastic band and adjustments are made by removing the silk ligature segments to achieve a flow reduction of 40-50%. Mechanical occlusions are carried out to insure that hyperemia is abolished. The segment in which the clot is formed is injured by squeezing it 3 or 4 times with a Debakey Forcep. Very fine mosquito clamps, with the serrations covered with plastic, are applied distal to the flow probe and proximal to the plastic occluder in order to isolate the segment and prevent leakage. Blood is withdrawn through the cannulated sidebranch. If some blood remains in the isolated segment, it is flushed antegrade with saline by opening the clamp near the distal occluder. Using the cannulated sidebranch, 0.1 ml thrombin (1000 U/ml) is injected into the isolated segment, followed by 0.3 ml blood removed from the jugular vein. The clot is allowed to "cure" for 15 minutes.

A blood sample is taken for measurement of PT (prothrombin time) and APTT (activated partial thromboplastin time). At the end of the 15 min period, the mosquito clamps are removed, proximal clamp first, distal clamp 2 min. later. If the flow meter still registers 0 flow, indicating the presence of an occlusive clot, 5000 U of heparin is given i.v., the side branch catheter is removed and the side branch is tied off. Additional doses of 1000 U of heparin are administered i.v. at hourly intervals after the initial dose of heparin, as required.

A blood sample is taken for measurement of platelet responsiveness, PT and APPT shortly after the first administration of heparin and at selected times as indicated below. After an additional 30 min. elapses during which the occlusive nature of the clot is confirmed, test compounds are administered (either by bolus injection or by beginning infusions, as appropriate and by the appropriate route), and an injection of 0.25 mg/kg t-PA is administered by i.v. bolus injection. Administration of t-PA is repeated every 15 min for up to one hour or until reperfusion occurs. Reperfusion is defined as the re-establishment of 50% of the amount of flow in the vessel prior to clot formation. Time to reperfusion is measured from the time of the first t-PA injection. A blood sample is taken at the time of the reperfusion for measurement of coagulation factors and platelet responsiveness.

Reocclusion is defined as the return of flow to 0 ml/min in the vessel and time to reocclusion is measured from the time of reperfusion. A final blood sample is obtained for measurement of coagulation factors and platelet responsiveness.

Animals are followed for 1-2 hours after lysis, depending on the physiological state of the animal.

Compounds are evaluated with regard to their ability to shorten the time to reperfusion, lengthen the time to reocclusion, or both.

Maximum effectiveness of a compound is defined as failure to reocclude for the duration of the test. Compounds may be less than maximally effective if they lead to a significant prolongation of the time required to achieve reocclusion after lysis. Such agents are considered for retesting using a different dosage regimen.

Figure 9:
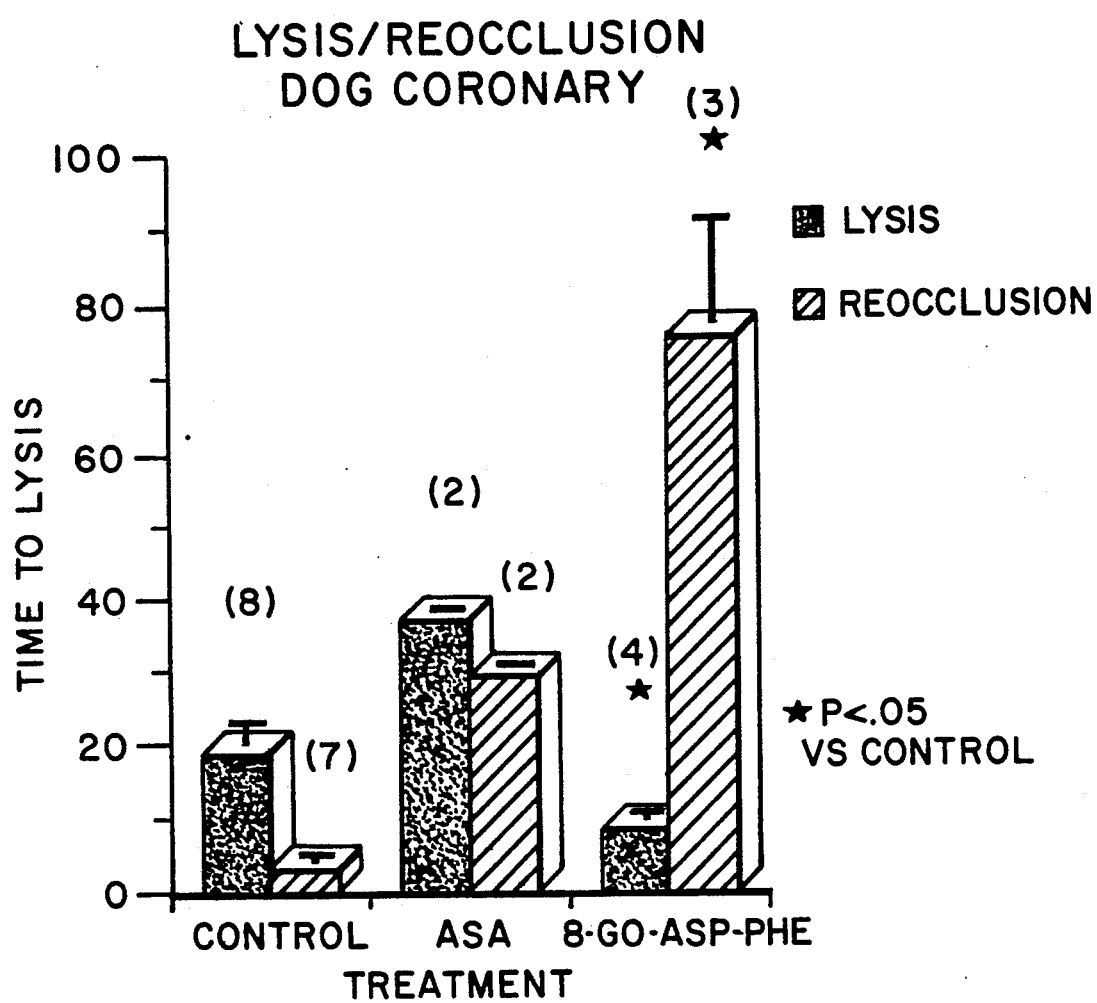
FIG. 9 shows the effect of 8-GO-Asp-Phe on reperfusion (lysis) and re-occlusion in time (min) upon co-administration with t-PA in dogs compared to control (without 8-GO-Asp-Phe) and ASA.

The results of the above test, using clinically available Genentech Activase t-PA, are set forth in the following Table 3 and in FIG. 9.

TABLE 3

| Treatment | Time to Lysis | SEM | N |
|---|---|---|---|
| A. Time to Lysis (minutes) | | | |
| Control | 18.4 | 2.9 | 8 |
| Aspirin (ASA) | 37.0 | — | 2 |
| 8-GO-Asp—Phe | 8.4 | 0.6 | 4 |
| Treatment | Time to Re-occlusion | SEM | N |
| B. Time to Re-occlusion (minutes) | | | |
| Control | 3.1 | 0.6 | 7 |
| Aspirin (ASA) | 29.0 | — | 2 |
| 8-GO-Asp—Phe | 75.7 | 14.3 | 3 |

SEM = Standard Error of the Mean.

The novel peptide mimetic compound of this invention can be used for administration to a mammalian host by conventional means, such as by parenteral or oral methods of administration, preferably in formulations with pharmaceutically acceptable diluents or carriers. The preferable route of administration as a platelet aggregation inhibitor is parenteral, e.g. intravenously. Intravenous administration of the peptide mimetic compound in solution with normal physiological saline, human albumin and other such diluents and carriers is illustrative. Other suitable formulations of the active peptide mimetic compound in pharmaceutically acceptable diluents and carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

The infusion rate required to completely inhibit platelet aggregation in the dog was approximately 20–30 μg/kg/min. Assuming that complete inhibition of platelet responsiveness is desired, about 43 mg/kg of the drug would be required per 24 hour period of infusion (~3g/day, total dose), if the platelet dose-response in dogs is directly scaled to humans. Duration of therapy may range from one to several days.

Various other examples will be apparent to the person skilled in the art after reading the present disclosure without departing from the spirit and scope of the invention. It is intended that all such examples be included within the scope of the appended claims.

What is claimed is:

1. N-[8-[(Aminoiminomethyl)amino]-1-oxooctyl]-N-L-α-aspartyl-L-phenylalanine.

2. A method of inhibiting platelet aggregation in a warm blooded mammal comprising administering to said mammal an effective amount for inhibiting platelet aggregation of the compound of claim 1 in a pharmaceutically acceptable carrier.

3. A method of inhibiting formation of a thrombus in a warm blooded mammal comprising administering to said mammal an effective amount for inhibiting thrombus formation of the compound of claim 1 in a pharmaceutically acceptable carrier.

4. A pharmaceutical composition which comprises a peptide mimetic compound of claim 1 in an amount effective for inhibiting platelet aggregation with a pharmaceutically acceptable carrier.

5. A method of enhancing the thrombolytic activity of tissue plasminogen activator administered to a warm blooded mammal comprising co-administering an effective amount of the compound of claim 1 suitable to shorten the time to reperfusion and to prolong the time to achieve re-occlusion.

* * * * *

UNITED STATES PATENT AND TRADEMARK OFFICE
CERTIFICATE OF CORRECTION

PATENT NO. : 5,053,393
DATED : October 1, 1991
INVENTOR(S) : NOVEL PLATELET AGGREGATION INHIBITOR It is certified that error appears in the above-identified patent and that said Letters Patent is hereby corrected as shown below:

At col. 3, line 59, "8-" should be cancelled. At col. 3, line 60, the symbol "⌴" should read --☐--. At col. 3, line 64, the symbol "⌴" should read --☐--. At col. 4, line 26, "4me" should read --4-me--. At col. 6, line 35, cancel "a".

Signed and Sealed this

Seventh Day of June, 1994

Attest:

BRUCE LEHMAN

Attesting Officer     Commissioner of Patents and Trademarks